(12) United States Patent
Dagsland (10) Patent No.: US 6,325,061 B1
(45) Date of Patent: Dec. 4, 2001

(54) INHALATION DEVICE

(75) Inventor: Allan Dagsland, Karlshamm (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/297,868

(22) PCT Filed: Mar. 30, 1999

(86) PCT No.: PCT/SE99/00529

§ 371 Date: May 10, 1999

§ 102(e) Date: May 10, 1999

(87) PCT Pub. No.: WO99/49918

PCT Pub. Date: Oct. 7, 1999

(30) Foreign Application Priority Data

Mar. 30, 1998 (SE) .................................................. 9801114

(51) Int. Cl.[7] .................................................. A61M 16/00
(52) U.S. Cl. .................................. 128/203.15; 128/203.12
(58) Field of Search ........................ 128/203.15–203.23, 128/200.14–200.16, 205.11, 203.12; 604/58, 56

(56) References Cited

U.S. PATENT DOCUMENTS

| | | | |
|---|---|---|---|
| 4,013,075 | 3/1977 | Cocozza | 128/266 |
| 4,069,819 | 1/1978 | Valentini et al. | 128/206 |
| 4,907,583 * | 3/1990 | Wetterlin et al. | 128/203.15 |
| 5,033,463 * | 7/1991 | Cocozza | 128/203.21 |
| 5,301,666 * | 4/1994 | Lerk et al. | 128/203.15 |
| 5,304,125 * | 4/1994 | Leith | 604/58 |
| 5,320,095 * | 6/1994 | Nijkerk et al. | 128/203.23 |
| 5,331,953 * | 7/1994 | Andersson et al. | 128/200.14 |
| 5,394,868 * | 3/1995 | Ambrosio et al. | 128/203.23 |
| 5,435,297 | 7/1995 | Klein | 128/200.23 |
| 5,437,271 * | 8/1995 | Hodson et al. | 128/203.15 |
| 5,505,196 * | 4/1996 | Herold et al. | 128/203.23 |
| 5,619,985 * | 4/1997 | Ohki et al. | 128/203.21 |
| 5,647,349 * | 7/1997 | Ohki et al. | 128/203.15 |
| 5,694,920 * | 12/1997 | Abrams et al. | 128/200.16 |
| 5,715,811 * | 2/1998 | Ohki et al. | 128/203.21 |
| 5,727,546 * | 3/1998 | Clarke et al. | 128/203.15 |
| 5,740,792 * | 4/1998 | Ashley et al. | 128/203.15 |
| 5,740,794 * | 4/1998 | Smith et al. | 128/203.15 |
| 5,785,049 * | 7/1998 | Smith et al. | 128/203.15 |
| 5,829,434 * | 11/1998 | Ambrosio et al. | 128/203.15 |
| 5,921,237 * | 7/1999 | Eisele et al. | 128/203.15 |
| 5,996,577 * | 12/1999 | Ohki et al. | 128/203.15 |
| 6,006,747 * | 12/1999 | Eisele et al. | 128/203.15 |
| 6,026,809 * | 2/2000 | Abrams et al. | 128/203.15 |
| 6,029,661 * | 2/2000 | Whaley et al. | 128/203.15 |
| 6,065,472 * | 5/2000 | Anderson et al. | 128/203.21 |
| 6,123,070 * | 9/2000 | Bruna et al. | 128/203.15 |
| 6,142,145 * | 11/2000 | Dagsland et al. | 128/203.15 |

FOREIGN PATENT DOCUMENTS

WO 94/14492    7/1994   (WO) .

* cited by examiner

Primary Examiner—John G. Weiss
Assistant Examiner—Teena Mitchell
(74) Attorney, Agent, or Firm—Fish & Richardson P.C.

(57) ABSTRACT

A powder inhaler for administering powder by inhalation, comprising a chamber (58) which includes a base member (12) and a peripheral wall member (48), wherein the chamber (58) includes a first inlet (36) through which a first stream of air containing powder is in use drawn on inhalation by a user and a plurality of second inlets (66, 67, 68, 69, 100) at the junction between the base member (12) and the peripheral wall member (48) through which a plurality of second streams of air of combined lesser flow than the first stream of air are in use drawn on inhalation by the user so as to minimize retention of powder at the junction between the base member (12) and the peripheral wall member (48).

22 Claims, 6 Drawing Sheets

INHALATION DEVICE

BACKGROUND OF THE INVENTION

The present invention relates to a powder inhaler for administering powder by inhalation.

A number of powder inhalers are known which use different systems for introducing a dose of powder into an air stream. Typically, the powder is inhaled into the lungs of a patient in order to treat, for example, asthma.

EP-A-0237507 discloses one such powder inhaler. This inhaler comprises an inhalation channel and a mouthpiece which includes an air chamber and an outlet nozzle, which together define a flow path through which a stream of air is drawn during inhalation by a user. This inhaler further comprises a dosing mechanism for providing a dose of powder to the inhalation channel. During inhalation, air is first drawn into and through the inhalation channel so as to pick up powder. The stream of air containing powder is then drawn through the air chamber and out of the outlet nozzle of the mouthpiece.

Figure 1:
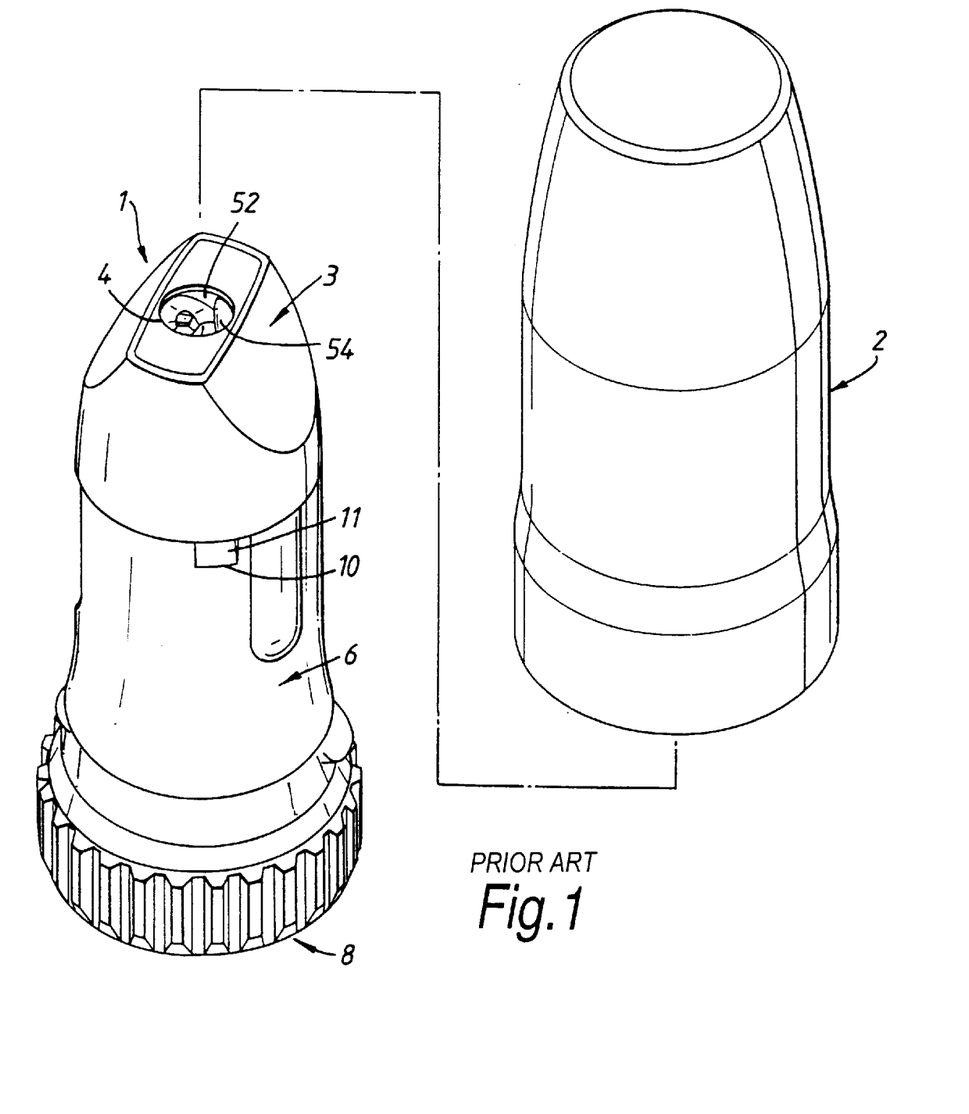
FIG. 1 illustrates a perspective view of a known powder inhaler, illustrated with the cap separated.

FIG. 1 illustrates such a powder inhaler. The inhaler comprises an inhaler unit 1 and a cap 2 which is a screw fit to the same. The inhaler unit 1 comprises a mouthpiece 3 which includes an outlet nozzle 4, an inhaler body 6 and a rotatable grip portion 8 for operating a dosing mechanism for providing doses of powder for inhalation. The inhaler body 6 is provided with an opening 10 which is filled with a window 11 through which an indicating wheel 42 is visible so as to provide an indication as to the usage of the inhaler.

Figure 2:
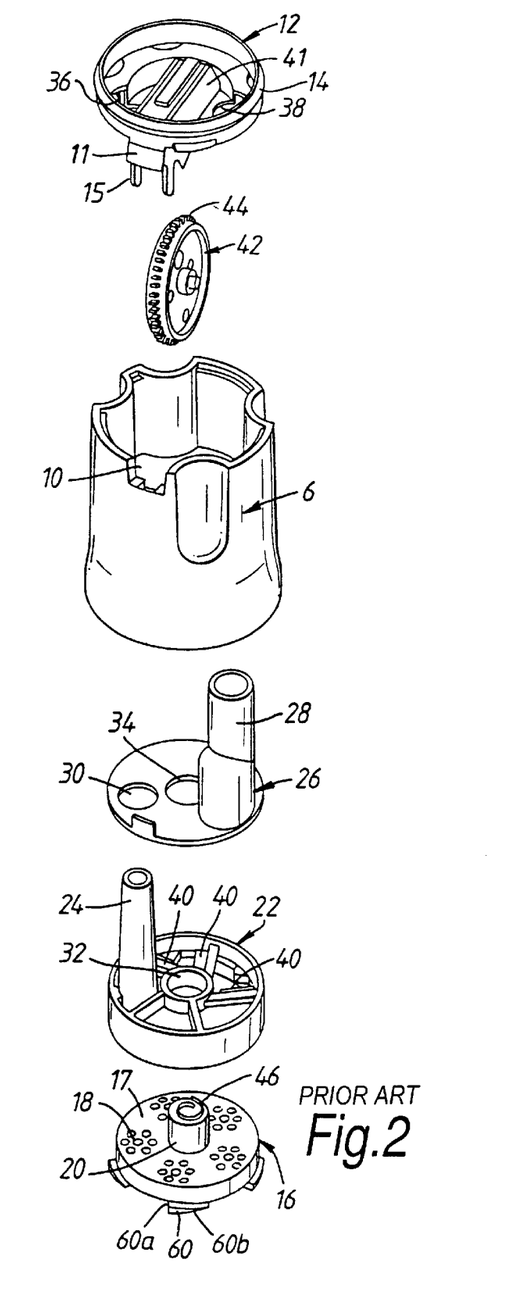
FIG. 2 illustrates an exploded perspective view of component parts of the inhaler of FIG. 1.
Figure 3:
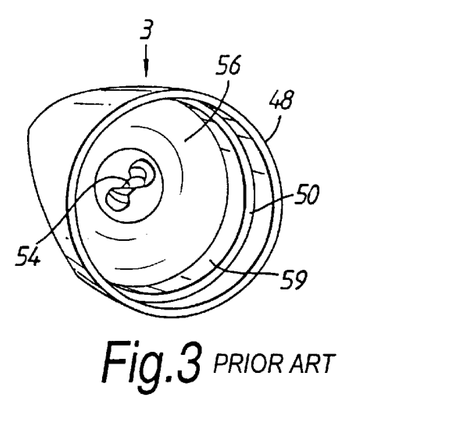
FIG. 3 illustrates the underside of the mouthpiece of the inhaler of FIG. 1.

FIG. 2 illustrates in exploded view component parts disposed within and to the inhaler body 6. The inhaler body 6 is capped with a divider 12 which is fixed thereto. For aesthetic reasons the inhaler body 6 is an opaque moulding. The divider 12 is a transparent moulding which includes a peripheral groove 13 and an adjacent peripheral ridge 14 by which the mouthpiece 3 is attached thereto. The divider 12 further includes a depending tongue 15, a part of which forms the window 11.

Within the inhaler body 6 are housed the component parts of the dosing mechanism. These component parts include a dosing unit 16 which comprises a member 17 having a planar surface in which a plurality of dosing elements 18 are provided and a s haft 20 which extends axially from the centre of the member 17, a distribution unit 22 which comprises an inhalation channel 24 and a storage unit 26 which comprises a storage chamber 28 for storing powder. The above-mentioned component parts of the dosing mechanism are assembled by passing the inhalation channel 24 through an opening 30 in the storage unit 26 and passing the shaft 20 through central openings 32, 34 in the distribution unit 22 and the storage unit 26 respectively. When so assembled, the upper ends of the inhalation channel 24 and the storage chamber 28 pass respectively through first and second openings 36, 38 in the divider 12. In this way, the distribution unit 22 and the storage unit 26 are fixed in position in relation to one another and the dosing unit 16 can be rotated relative thereto.

In this inhaler the storage chamber 28 is open at the bottom such that in use powder is provided to the dosing unit 16 under the action of gravity and the distribution unit 22 further comprises scrapers 40 which are resiliently biased against the surface of the member 17 of the dosing unit 16 in which the dosing elements 18 are provided. In this way, as the dosing unit 16 is rotated, the dosing elements 18, which in this inhaler comprise a plurality of through holes, are filled with powder by the scrapers 40. Powder is prevented from passing through the dosing elements 18 by a plate (not illustrated) which is disposed beneath the dosing unit 16.

The divider 12 further includes a supporting member 41 for rotatably supporting an indicating wheel 42. The indicating wheel 42 includes a plurality of teeth 44 disposed around the periphery thereof which engage with a spiral groove or protrusion 46 on the end face of the shaft 20 of the dosing unit 16. The supporting member 41 is configured to align the indicating wheel 42 such that a part of the periphery thereof is disposed adjacent the inner surface of the window 11. In use, as the dosing unit 16 is rotated, the spiral groove or protrusion 46 engages with one or more of the teeth 44 on the indicating wheel 42 so as to rotate the same. In this way, by providing a coloured marking on the periphery of the indicating wheel 42, it is possible to provide the user with a visible indication at the window 11 as to the usage of the inhaler.

Figure 4:
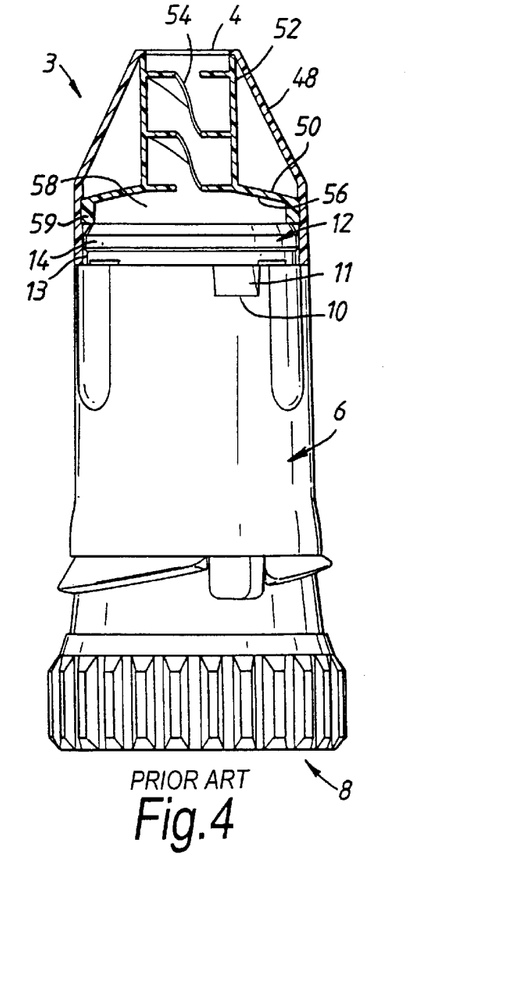
FIG. 4 illustrates a part-sectional side view of the inhaler of FIG. 1.

As illustrated in FIG. 4, the mouthpiece 3 is fixed to the divider 12. The mouthpiece 3 comprises first and second parts 48, 50, the first part 48 being the part which is gripped in the lips of a user and the second part 50 being an insert fitted within the first part 48. The second part 50 comprises a tubular section 52 which includes one or more spirally or helically shaped projections 54 that act to deflect the air drawn therethrough and thereby deagglomerate any larger particles of entrained powder and a substantially radially-directed flange 56 which provides a surface that together with upper surface of the divider 12 defines an air chamber 58 that is in fluid communication with the inhalation channel 24 through which air containing powder is drawn on inhalation by a user. The flange 56 includes a downwardly-depending annular skirt 59 which is a tight fit within the first part 48 and acts to fix the second part 50 to the first part 48.

In use, as described hereinabove, powder is transferred from the storage chamber 28 to one of the dosing elements 18, and, with rotation of the dosing unit 16, the one dosing element 18 provides a dose of powder to the inhalation channel 24. In this inhaler the dosing unit 16 is rotated by rotating the grip portion 8 in the clockwise sense when viewed from below between first and second angularly-spaced positions. For this purpose, the dosing unit 16 includes wedge-shaped elements 60 disposed around the periphery of the member 17 thereof and the grip portion 8 comprises a resilient member (not illustrated) which is configured to engage with an axially-directed surface 60a of a respective one of the wedge-shaped elements 60 so as to rotate the dosing unit 16 by pushing the respective wedge-shaped element 60. On rotation of the grip portion 8 in the opposite, counter-clockwise sense between the second and the first angularly-spaced positions, the dosing unit 16 remains stationary and the resilient member is located behind the axially-directed surface 60a of the adjacent wedge-shaped element 60; the resilient member riding over an inclined surface 60b of the adjacent wedge-shaped element 60.

SUMMARY OF THE INVENTION

Whilst this powder inhaler functions perfectly adequately, it is an aim of the present invention further to improve the transfer of powder through the air chamber.

Accordingly, the present invention provides a powder inhaler for administering powder by inhalation, comprising a chamber which includes a base member and a peripheral wall member, wherein the chamber includes a first inlet through which a first stream of air containing powder is in use drawn on inhalation by a user and a plurality of second inlets at the junction between the base member and the peripheral wall member through which a plurality of second streams of air of combined lesser flow than the first stream of air are in use drawn on inhalation by the user so as to minimise retention of powder at the junction between the base member and the peripheral wall member.

In this way, the supplementary streams of air drawn through the second inlets pass over an inner peripheral surface of the chamber, preferably along the peripheral wall member towards the outlet thereof. These supplementary streams of air ensure that there are no dead spots or stagnant regions in the chamber. As a result, the likelihood of any retention of powder in the chamber is greatly reduced.

Preferably, the chamber includes a third inlet through which a third stream of air is in use drawn into the chamber on inhalation by the user.

More preferably, the third inlet is in the base member of the chamber.

Preferably, the first and third inlets are disposed to one side of the chamber.

In this way, the streams of air drawn through the first and third inlets interact particularly effectively and good flow characteristics are achieved in the chamber.

Preferably, the base member and the peripheral wall member are separate components which are attached to one another and the second inlets comprise channels in one or both of the base member and the peripheral wall member.

Providing supplementary streams of air by means of such channels is particularly advantageous since it is only necessary to make minor alterations to the shape of the component parts. Further, additional dedicated openings are unnecessary. In addition, such channels necessarily provide streams of air at the junction between the base member and the peripheral wall member of the chamber where stagnant regions are most likely to occur.

More preferably, the channels comprise recesses in an outer peripheral edge of the base member.

Preferably, the plurality of second inlets are disposed in a peripheral region of the chamber remote from the first inlet.

In a preferred embodiment the first inlet is disposed to one side of the chamber and the plurality of second inlets are disposed to the generally opposite side of the chamber.

In this way, the regions of the chamber, in which the stream of air drawn through the first inlet is not likely to pass directly, are provided with streams of air drawn through the second inlets.

Preferably, the inhaler further comprises a powder dislodging member disposed within the chamber for dislodging powder from an inner surface thereof and wherein at least one of the plurality of second inlets is disposed adjacent the powder dislodging member so as to minimise retention of powder thereon.

As stagnant regions are likely to develop near the powder dislodging member, these stagnant regions can be prevented and retention reduced by providing at least one of the plurality of second inlets near the powder dislodging member.

More preferably, the inhaler further comprises a cover plate which covers the base member and includes at an outer peripheral edge thereof at least one channel which generally positionally corresponds to the plurality of second inlets.

In a preferred embodiment the cover plate includes the powder dislodging member.

As should be understood, the function of the second inlets is not for the mixing or deagglomeration of powder, but merely to prevent stagnant regions or dead spots developing in the chamber. As such, the second inlets need only allow a relatively small amount of air through into the chamber.

Preferably, the plurality of second inlets are configured such that from 10 to 40 percent of the air drawn into the chamber is drawn therethrough.

More preferably, the plurality of second inlets are configured such that from 20 to 35 percent of the air drawn into the chamber is drawn therethrough.

Still more preferably, the plurality of second inlets are configured such that from 25 to 30 percent of the air drawn into the chamber is drawn therethrough.

Preferably, the inhaler further comprises a housing, one end of which provides the base member, which includes at least one groove which is in fluid communication with the plurality of second inlets.

Preferably, the at least one groove extends circumferentially.

Preferably, the housing includes at least one flute which is in fluid communication with the at least one groove.

More preferably, the at least one flute is disposed in an outer surface of the housing.

In a preferred embodiment the housing includes a plurality of grooves and a plurality of flutes which are in fluid communication with respective ones of the plurality of second inlets.

With this configuration, air is easily and efficiently drawn from the atmosphere into the chamber.

Preferably, the peripheral wall member includes at least one inwardly-extending flange which is clipped over the peripheral ridge of the base member.

Preferably, the base member is circular, the peripheral wall member is rotatable around the base member and the peripheral wall member includes a plurality of inwardly-extending flanges which are spaced and dimensioned such that at least three-quarters of the cross-sectional area of the second inlets is open for any relative position of the base member and the peripheral wall member.

In this way, the peripheral wall member, which may form part of the mouthpiece, can be freely rotated without interfering with the function of the second inlets. At the same time, the flanges hold the peripheral wall member securely in place.

Medicaments suitable for administration by the powder inhaler of the present invention are any which may be delivered by inhalation and include, for example, β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

Preferred embodiments of the present invention will now be described hereinbelow by way of example only with reference to the accompanying drawings.

DETAILED DESCRIPTION OF THE INVENTION

Structurally, the powder inhalers in accordance with the preferred embodiments of the present invention have many features in common with the known powder inhaler described hereinabove in relation to FIGS. 1 to 4. For this reason, and in order to avoid unnecessary duplication of description, only the structural differences will be described in detail and reference is made to the preceding description of the known powder inhaler; like reference signs designating like parts.

Figure 5:
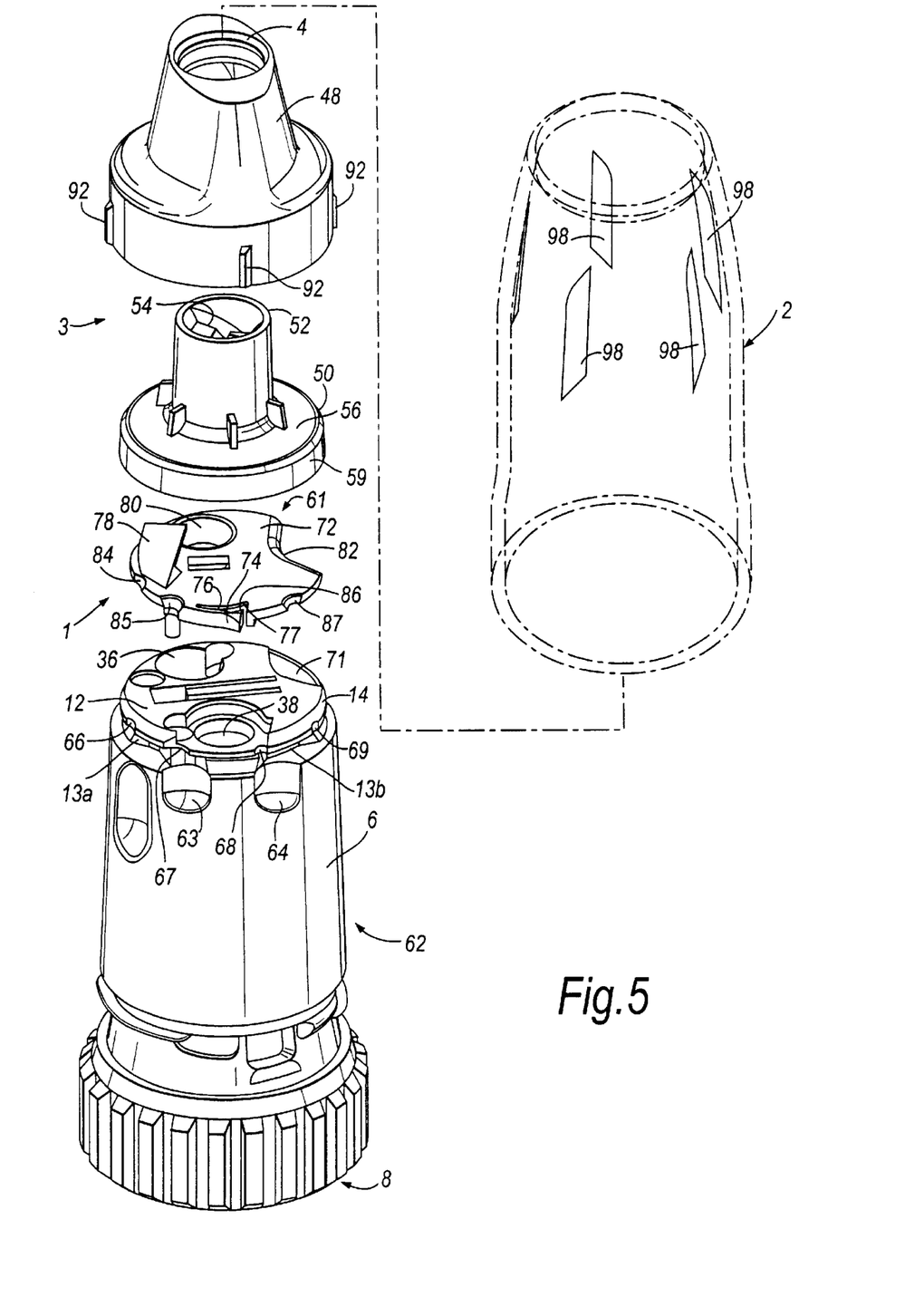
FIG. 5 illustrates an exploded perspective view of a powder inhaler in accordance with a first embodiment of the present invention, illustrated with the cap separated.
Figure 6:
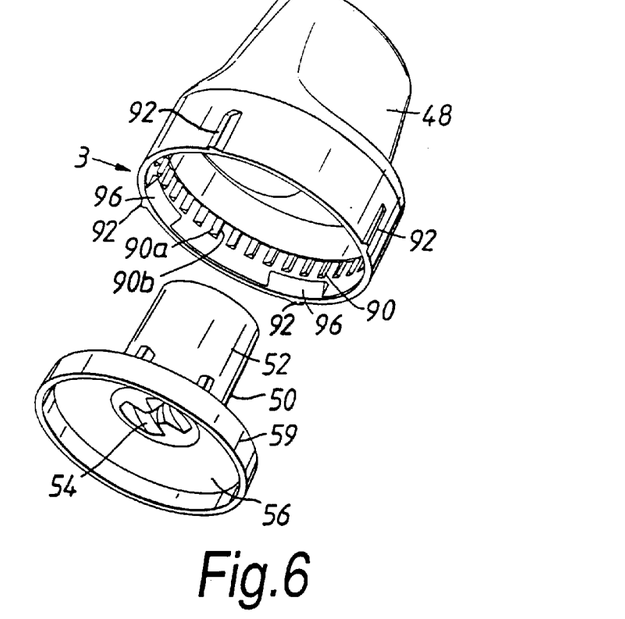
FIG. 6 illustrates an exploded perspective view of the component parts of the mouthpiece of the inhaler of FIG. 5.
Figure 7:
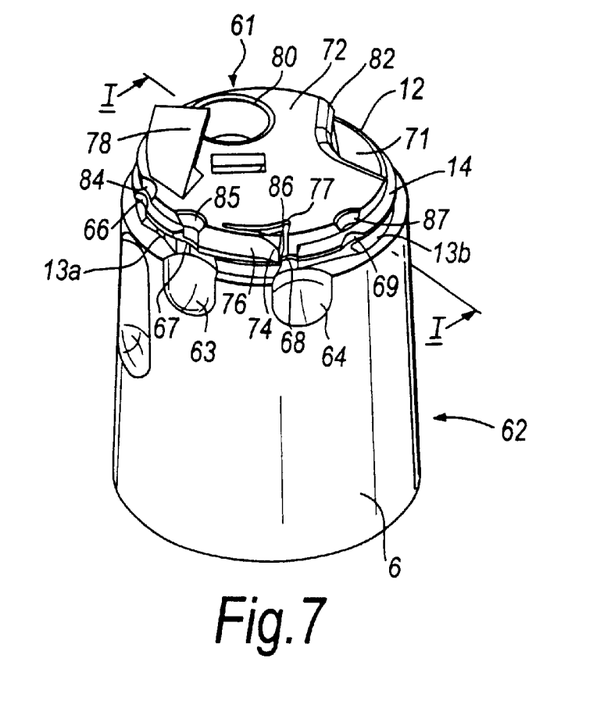
FIG. 7 illustrates a perspective view of the body part and the cover plate of the inhaler of FIG. 5.

FIGS. 5 to 7 illustrate a powder inhaler or components thereof in accordance with a first embodiment of the present invention. This embodiment is a modification of the above-described known powder inhaler and differs from the above-described known powder inhaler in the construction of the mouthpiece 3, the inhaler body 6 and the divider 12 and in further comprising a cover plate 61 which is disposed over the divider 12.

In this embodiment the inhaler unit 1 comprises a body part 62 which is a single component of an opaque material that comprises both the inhaler body 6 and the divider 12.

As in the above-described known powder inhaler, the inhaler body 6 includes the opening through which the indicating wheel 42 is visible, with the storage unit 26 being modified in comprising a tongue and being formed of a transparent material, one part, in this embodiment the distal end, of which tongue is shaped and dimensioned such that when the storage unit 26 is fitted in the inhaler body 6 that part of the tongue fills the opening 10 so as to provide the window 11. Further, as in the above-described known powder inhaler, the indicating wheel 42 is rotatably supported to the underside of the divider 12 such that at least a part of the periphery of the indicating wheel 42 is visible through the window 11.

The inhaler body 6 of this embodiment differs from that of the above-described known powder inhaler in including first and second flutes 63, 64 at the upper edge and outer surface thereof which are normally in fluid communication with the atmosphere.

As in the above-described known powder inhaler, the divider 12 includes a peripheral ridge 14 by which the mouthpiece 3 is attached to the body part 62. The divider 12 of this embodiment differs from that of the above-described known powder inhaler in including first and second peripherally-extending grooves 13a, 13b which together extend around a major part of the periphery of the divider 12 adjacent the peripheral ridge 14 and are in fluid communication with the first and second flutes 63, 64 in the inhaler body 6 respectively. The divider 12 of this embodiment further differs from that of the above-described known powder inhaler in that the peripheral ridge 14 includes first to fourth channels 66, 67, 68, 69, in this embodiment in the form of concave recesses at the outer peripheral edge of the peripheral ridge 14, with the first and second channels 66, 67 being in fluid communication with the first groove 13a and the third and fourth channels 68, 69 being in fluid communication with the second groove 13b. The channels 66, 67, 68, 69 in the peripheral ridge 14 provide air flow paths through which controlled amounts of air are, on inhalation by the user, drawn from the atmosphere into the air chamber 58 at the periphery thereof. In this embodiment the channels 66, 67, 68, 69 in the peripheral ridge 14 are disposed generally diametrically opposite the outlet to the inhalation channel 24 which is that region of the air chamber 58 in which stagnant volumes are most likely to exist. The divider 12 of this embodiment further differs from that of the above-described known powder inhaler in including a supplementary air inlet 71 which is in fluid communication with the atmosphere, in a preferred embodiment through an opening in the peripheral wall of the inhaler body 6.

The cover plate 61 comprises a substantially planar member 72 which covers the relatively complex structural features at the upper surface of the divider 12, a radially outwardly-biased catch element 74 which is connected to the planar member 72 by a resilient arm 76 and radially movably disposed in a peripheral recess 77 and a powder dislodging member 78, in this embodiment a scraper, which is configured to contact a part of the lower surface of the flange 56 which defines the upper surface of the air chamber 58. In this embodiment the cover plate 61 is of a smaller radial dimension than the peripheral edge of the peripheral ridge 14 of the divider 12. The cover plate 61 further includes first and second openings 80, 82 which correspond in position respectively to the outlet of the inhalation channel 24 and the supplementary air inlet 71 and first to fourth channels 84, 85, 86, 87 which are disposed at the outer peripheral edge thereof and correspond in position to the first to fourth channels 66, 67, 68, 69 in the peripheral ridge 14 of the divider 12. By providing channels 84, 85, 86, 87 in the cover plate 61, air flow paths are ensured between the channels 66, 67, 68, 69 in the peripheral ridge 14 of the divider 12 and the air chamber 58, which flow paths could be blocked if, for example, the manufacturing tolerances of the mouthpiece 3 were such that a peripherally-extending part of the mouthpiece 3 were to abut the peripheral edge of the upper surface of the cover plate 61. In this embodiment the first to fourth channels 84, 85, 86, 87 in the cover plate 61 are disposed upstream, in a rotational sense, of the powder dislodging member 78 such as to provide an air flow at a peripheral region of the air chamber 58 behind the powder dislodging member 78, which peripheral region is that region where powder dislodged by the powder dislodging member 78 would preferentially accumulate. In this embodiment one, the third, channel 86 in the cover plate 61 is provided by the recess 77 in which the catch element 74 is movably disposed and the other, the first, second and fourth, channels 84, 86, 87 comprise concave recesses at the outer peripheral edge of the cover plate 61. With this configuration, the channels 84, 85, 86, 87 in the cover plate 61 act to communicate air drawn through the channels 66, 67, 68, 69 in the peripheral ridge 14 of the divider 12 to the periphery of the air chamber 58. In this embodiment the effective total length of the first to fourth channels 84, 85, 86, 87 in the cover plate 61 is about one-quarter of the length of the peripheral edge of the cover plate 61.

Figure 8:
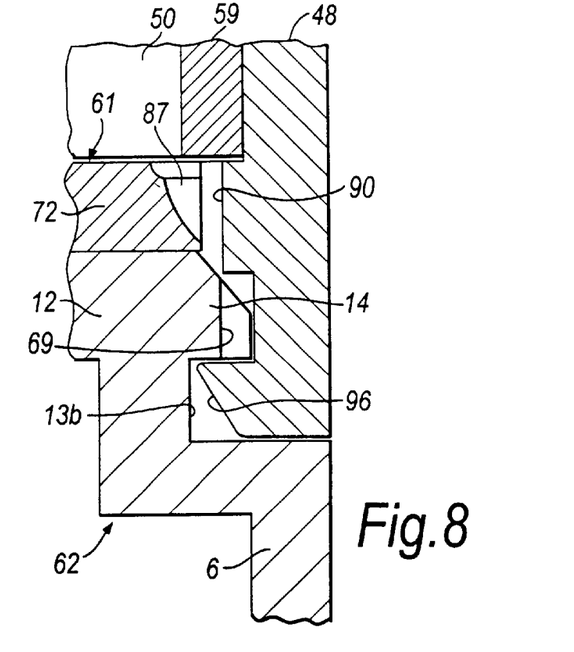
FIG. 8 illustrates a fragmentary vertical sectional view (along section I—I in FIG. 7) of the inhaler of FIG. 5.
Figure 9:
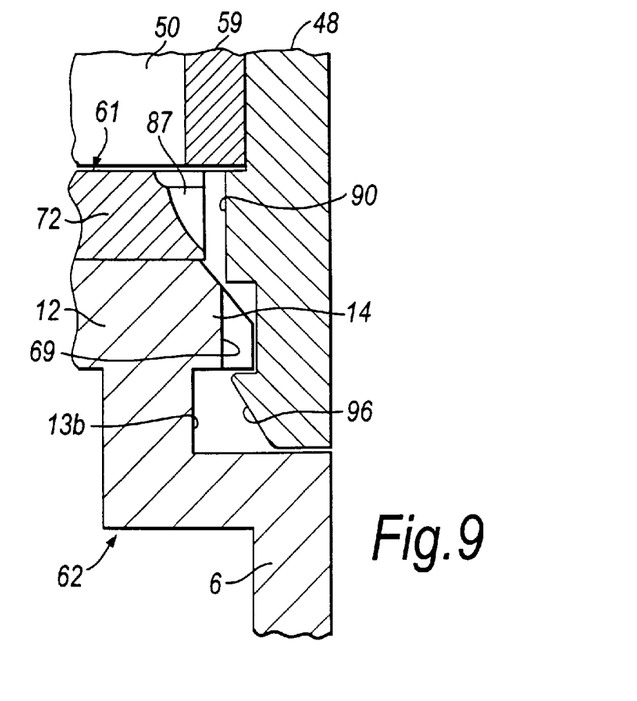
FIG. 9 illustrates a fragmentary vertical sectional view (along section I—I in FIG. 7) of the inhaler of FIG. 5 with a modified mouthpiece.

In this embodiment, similarly to the above-described known powder inhaler, the mouthpiece 3 comprises first and second parts 48, 50. The mouthpiece 3 of this embodiment differs from that of the above-described known powder inhaler in that the mouthpiece 3 is rotatable relative to the body part 62 and in that the first part 48 further includes a plurality of radially inwardly-directed projections 90 and a plurality of radially outwardly-directed projections 92. Each of the inwardly-directed projections 90 comprises a first flank 90a which faces in one sense, in this embodiment in the counter-clockwise sense when viewed from above, and a second flank 90b which faces in the opposite, clockwise sense. The inwardly-directed projections 90 act by engagement with the catch element 74 on the cover plate 61 to prevent the mouthpiece 3 from being freely rotated relative to the inhaler body 6, which free movement would be undesirable when a user was trying to grip the mouthpiece 3 in the lips. In order to rotate the mouthpiece 3 a sufficient rotational moment has to be applied thereto such as to cause the catch element 74 to ride over the inwardly-directed projections 90 on the mouthpiece 3. In use, on rotating the mouthpiece 3 relative to the body part 62, the lower surface of the flange 56 of the second part 50 of the mouthpiece 3 is rotated relative to the powder dislodging member 78, thereby causing any powder which may have accumulated on that part of the lower surface of the flange 56 immediately upstream, in a rotational sense, of the powder dislodging member 78 to be removed. The mouthpiece 3 of this embodiment further differs from that of the above-described known powder inhaler in that the first part 48 thereof further comprises a plurality of radially inwardly-directed flanges 96 disposed about the lower edge thereof by which the mouthpiece 3 is clipped to the divider 12; the inwardly-directed flanges 96 being clipped beneath the lower surface of the peripheral ridge 14 of the divider 12. In this embodiment, as illustrated in FIG. 8, where the flanges 96 have a radial width such as to extend to the inner radial edge of the channels 66, 67, 68, 69 in the peripheral ridge 14 of the divider 12, the flanges 96 are peripherally spaced such that at least three of the channels 66, 67, 68, 69 in the peripheral ridge 14 of the divider 12 are in fluid communication with a respective one of the first and second grooves 13a, 13b for any relative position of the mouthpiece 3 and the body part 62. In a modified mouthpiece 3, as illustrated in FIG. 9, the flanges 96 can be configured so as to have a smaller radial width such as to extend only partially over the channels 66, 67, 68, 69 in the peripheral ridge 14 of the divider 12. In this modified mouthpiece 3 the flanges 96 need not have any particular peripheral spacing and indeed the mouthpiece 3 could include a single, continuous flange.

The cap 2 of this embodiment differs from the cap 2 of the above-described known powder inhaler in being configured to rotate the mouthpiece 2 on removal. In this embodiment the cap 2 includes a plurality of resilient members 98 disposed about the inner periphery thereof which engage with the outwardly-directed projections 92 on the first part 48 of the mouthpiece 3. The resilient members 98 extend axially and enclose an acute angle with the inner periphery of the cap 2; the distal ends of the resilient members 98 being directed in the counter-clockwise sense when viewed from above. By having an axial length the resilient members 98 engage the outwardly-directed projections 92 on the first part 48 of the mouthpiece 3 for the entire period that the cap 2 is being removed, in this embodiment by unscrewing in the counter-clockwise sense when viewed from above. In use, when the cap 2 is removed, one or more of the resilient members 98 engage respective outwardly-directed projections 92 on the first part 48 of the mouthpiece 3 and cause the mouthpiece 3 to be rotated relative to the body part 62, thereby causing the powder dislodging member 78 to remove any powder which may have accumulated on that part of the lower surface of the flange 56 of the second part 50 of the mouthpiece 3 upstream, in a rotational sense, of the powder dislodging member 78. In this way, whenever a user removes the cap 2 the mouthpiece 3 is automatically rotated. In fitting the cap 2, in this embodiment by screwing in the opposite, clockwise sense, the resilient members 98 are deflected and ride over the respective outwardly-directed projections 92 on the first part 48 of the mouthpiece 3.

Figure 10:
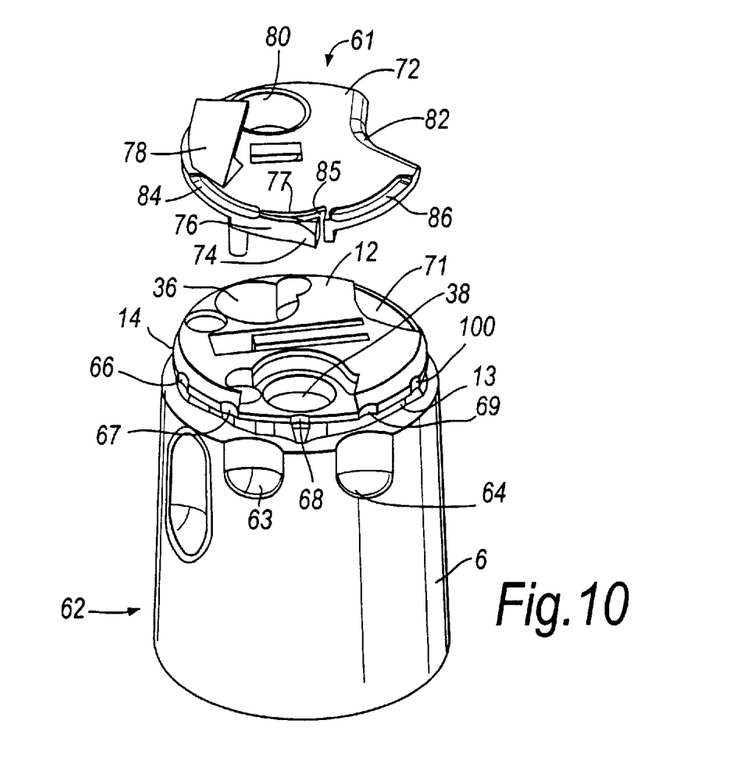
FIG. 10 illustrates an exploded perspective view of the body part and the cover plate of an inhaler in accordance with a second embodiment of the present invention.
Figure 11:
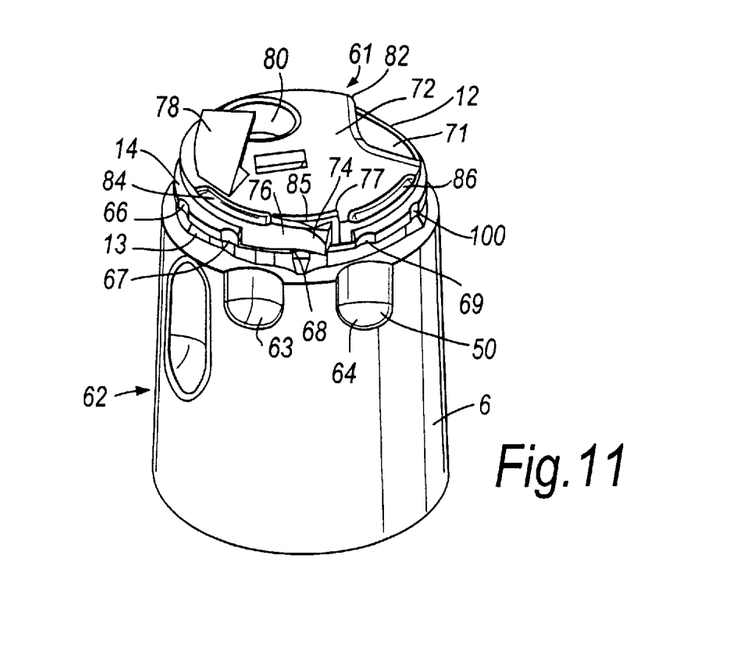
FIG. 11 illustrates a perspective view of the body part and the cover plate of the inhaler of FIG. 10.

FIGS. 9 and 10 illustrate component parts of a powder inhaler in accordance with a second embodiment of the present invention. This embodiment is a modification of the inhaler of the above-described first embodiment and differs from the first embodiment in the construction of the divider 12 and the cover plate 61. The divider 12 of this embodiment differs from the divider 12 of the first embodiment in including a single peripheral groove 13 adjacent the peripheral ridge 14 thereof and in that the peripheral ridge 14 includes first to fifth channels 66, 67, 68, 69, 100. As in the first embodiment, the channels 66, 67, 68, 69, 100 in the peripheral ridge 14 comprise concave recesses at the outer peripheral edge of the peripheral ridge 14. The cover plate 61 of this embodiment differs from the cover plate 61 of the first embodiment in including first to third channels 84, 85, 86. As in the first embodiment, in this embodiment one, the second, channel 85 in the cover plate 61 is provided by the recess 77 in which the catch element 74 is movably disposed. The cover plate 61 of this embodiment further differs from the cover plate 61 of the first embodiment in that the first and third channels 84, 86 comprise elongate recesses which extend along the peripheral edge of the cover plate 61. In this embodiment the first, second and third channels 84, 85, 86 in the cover plate 61 are disposed adjacent one another and the effective total length of the first, second and third channels 84, 85, 86 is about one-third of the length of the peripheral edge cover plate 61.

Finally, it will be understood that the present invention has been described in its preferred embodiments and can be modified in many different ways without departing from the scope of the appended claims.

What is claimed is:

1. A powder inhaler for administering powder by inhalation, comprising a powder delivery component including a multiple-does storage region and a mechanism for accessing a single dose at a time from said storage region, an inhalation channel that is positioned to receive powder from said mechanism of said powder delivery component so as to provide a first stream of air containing powder when air is drawn through said inhalation channel, a chamber which includes a base member and a peripheral wall member, said base member having a transverse surface extending across said peripheral wall member, wherein the chamber includes a first inlet through said surface through which said first stream of air containing powder is in use drawn into said chamber on inhalation by a user and a plurality of second inlets at the junction between the base member and the peripheral wall member at said surface through which a plurality of second streams of air of combined lesser flow than the first stream of air are in use drawn on inhalation by a user so as to minimize retention of powder at the junction between the base member and the peripheral wall member at said surface.

2. The inhaler of claim 1, wherein the chamber includes a third inlet through which a third stream of air is in use drawn into the chamber on inhalation by a user.

3. The inhaler of claim 2, wherein the third inlet is in the base member of the chamber.

4. A powder inhaler for administering powder by inhalation, comprising a powder delivery component, an inhalation channel that is positioned to receive powder from said powder delivery component so as to provide a first stream of air containing powder when air is drawn through said inhalation channel, a chamber which includes a base member and a peripheral wall member, wherein the chamber includes a first inlet through which said first stream of air containing powder is in use drawn on inhalation by a user and a plurality of second inlets at the junction between the base member and the peripheral wall member through which a plurality of second streams of air of combined lesser flow than the first stream of air are in use drawn on inhalation by a user so as to minimize retention of powder at the junction between the base member and the peripheral wall member, wherein the chamber includes a third inlet through which a third stream of air is in use drawn into the chamber on inhalation by a user, wherein the first and third inlets are disposed to one side of the chamber.

5. The inhaler of claim 1, wherein the base member and the peripheral wall member are separate components which are attached to one another and the second inlets comprise channels in one or both of the base member and the peripheral wall member.

6. A powder inhaler for administering powder by inhalation, comprising a powder delivery component, an inhalation channel that is positioned to receive powder from said powder delivery component so as to provide a first stream of air containing powder when air is drawn through said inhalation channel, a chamber which includes a base member and a peripheral wall member, wherein the chamber includes a first inlet through which said first stream of air containing powder is in use drawn on inhalation by a user and a plurality of second inlets at the junction between the base member and the peripheral wall member through which a plurality of second streams of air of combined lesser flow than the first stream of air are in use drawn on inhalation by a user so as to minimize retention of powder at the junction between the base member and the peripheral wall member, wherein the base member and the peripheral wall member are separate components which are attached to one another and the second inlets comprise channels in one or both of the base member and the peripheral wall member, wherein the channels comprise recesses in an outer peripheral edge of the base member.

7. The inhaler of claim 6, wherein the outer peripheral edge of the base member comprises an outwardly-extending peripheral ridge to which the peripheral wall member is attached.

8. A powder inhaler for administering powder by inhalation, comprising a powder delivery component, an inhalation channel that is positioned to receive powder from said powder delivery component so as to provide a first stream of air containing powder when air is drawn through said inhalation channel, a chamber which includes a base member and a peripheral wall member, wherein the chamber includes a first inlet through which said first stream of air containing powder is in use drawn on inhalation by a user and a plurality of second inlets at the junction between the base member and the peripheral wall member through which a plurality of second streams of air of combined lesser flow than the first stream of air are in use drawn on inhalation by a user so as to minimize retention of powder at the junction between the base member and the peripheral wall member, further comprising a housing, one end of which provides the base member, which includes at least one groove which is in fluid communication with the plurality of second inlets.

9. The inhaler of claim 8, wherein the at least one groove extends about the periphery of the housing.

10. The inhaler of claim 8, wherein the housing includes at least one flute which is in fluid communication with the at least one groove.

11. The inhaler of claim 10, wherein the at least one flute is disposed in an outer surface of the housing.

12. The inhaler of claim 10, wherein the housing includes a plurality of grooves and a plurality of flutes which are in fluid communication with respective ones of the plurality of second inlets.

13. A powder inhaler for administering powder by inhalation, comprising a powder delivery component, an inhalation channel that is positioned to receive powder from said powder delivery component so as to provide a first stream of air containing powder when air is drawn through said inhalation channel, a chamber which includes a base member and a peripheral wall member, wherein the chamber includes a first inlet through which said first stream of air containing powder is in use drawn on inhalation by a user and a plurality of second inlets at the junction between the base member and the peripheral wall member through which a plurality of second streams of air of combined lesser flow than the first stream of air are in use drawn on inhalation by a user so as to minimize retention of powder at the junction between the base member and the peripheral wall member, wherein the plurality of second inlets are disposed in a peripheral region of the chamber remote from the first inlet.

14. The inhaler of claim 13, wherein the first inlet is disposed to one side of the chamber and the plurality of second inlets are disposed to the generally opposite side of the chamber.

15. A powder inhaler for administering powder by inhalation, comprising a powder delivery component, an inhalation channel that is positioned to receive powder from said powder delivery component so as to provide a first stream of air containing powder when air is drawn through said inhalation channel, a chamber which includes a base member and a peripheral wall member, wherein the chamber includes a first inlet through which said first stream of air containing powder is in use drawn on inhalation by a user and a plurality of second inlets at the junction between the base member and the peripheral wall member through which a plurality of second streams of air of combined lesser flow than the first stream of air are in use drawn on inhalation by a user so as to minimize retention of powder at the junction between the base member and the peripheral wall member, further comprising a powder dislodging member disposed within the chamber for dislodging powder from an inner surface thereof and wherein at least one of the plurality of second inlets is disposed adjacent the powder dislodging member.

16. The inhaler of claim 15, wherein the channels comprise recesses in an outer peripheral edge of the base member and, further comprising a cover plate which covers the base member and includes at an outer peripheral edge thereof at least one channel which generally positionally corresponds to the plurality of second inlets.

17. The inhaler of claim 16, wherein the cover plate includes the power dislodging member.

18. The inhaler of claim 8, wherein the outer peripheral edge of the base member comprises an outwardly-extending peripheral ridge to which the peripheral wall member is attached, wherein the peripheral wall member includes at least one inwardly-extending flange which is clipped over the peripheral ridge of the base member.

19. The inhaler of claim 18, wherein the base member is circular, the peripheral wall member is rotable around the base member and the peripheral wall member includes a plurality of inwardly-extending flanges which are spaced and dimensioned such that at least three-quarters of the cross-sectional area of the second inlets is open for any relative position of the base member and the peripheral wall member.

20. A powder inhaler for administering powder by inhalation, comprising a powder delivery component, an inhalation channel that is positioned to receive powder from said powder delivery component so as to provide a first stream of air containing powder when air is drawn through said inhalation channel, a chamber which includes a base member and a peripheral wall member, wherein the chamber includes a first inlet through which said first stream of air containing powder is in use drawn on inhalation by a user and a plurality of second inlets at the junction between the base member and the peripheral wall member through which a plurality of second streams of air of combined lesser flow than the first stream of air are in use drawn on inhalation by a user so as to minimize retention of powder at the junction between the base member and the peripheral wall member, wherein the plurality of second inlets are configured such that from 10 to 40 percent of the air drawn into the chamber is drawn therethrough.

21. The inhaler of claim 20, wherein the plurality of second inlets are configured such that from 20 to 35 percent of the air drawn into the chamber is drawn therethrough.

22. The inhaler of claim 21, wherein the plurality of second inlets are configured such that from 25 to 30 percent of the air drawn into the chamber is drawn therethrough.

* * * * *